United States Patent
Mesters

(10) Patent No.: US 7,067,680 B2
(45) Date of Patent: Jun. 27, 2006

(54) PROCESS FOR PREPARING ORGANIC HYDROPEROXIDE HAVING A REDUCED AMOUNT OF CONTAMINANTS

(75) Inventor: Carolus Matthias Anna Maria Mesters, Amsterdam (NL)

(73) Assignee: Shell Oil Company, Houston, TX (US)

(*) Notice: Subject to any disclaimer, the term of this patent is extended or adjusted under 35 U.S.C. 154(b) by 103 days.

(21) Appl. No.: 10/451,938

(22) PCT Filed: Dec. 17, 2001

(86) PCT No.: PCT/EP01/14992

§ 371 (c)(1), (2), (4) Date: Jun. 26, 2003

(87) PCT Pub. No.: WO02/051801

PCT Pub. Date: Jul. 4, 2002

(65) Prior Publication Data

US 2004/0063978 A1    Apr. 1, 2004

(30) Foreign Application Priority Data

Dec. 27, 2000    (EP) ................... 00311709

(51) Int. Cl.
- *C07D 317/49* (2006.01)
- *C07C 37/68* (2006.01)
- *B01J 35/10* (2006.01)
- *C10G 45/00* (2006.01)

(52) U.S. Cl. .............. 549/525; 549/542; 568/754; 208/251 H; 208/251 R

(58) Field of Classification Search ............ 549/542, 549/525; 208/251 H, 251 R; 568/754
See application file for complete search history.

(56) References Cited

U.S. PATENT DOCUMENTS

| 4,539,101 A | 9/1985 | Oleck et al. |
| 4,601,998 A * | 7/1986 | Oleck et al. ............ 502/318 |
| 5,723,637 A | 3/1998 | Tsuji et al. |
| 5,883,268 A | 3/1999 | Lin et al. |

FOREIGN PATENT DOCUMENTS

| EP | 0 345 856 | 12/1989 |
| WO | 99/42425 | 8/1999 |
| WO | 99/42426 | 8/1999 |

OTHER PUBLICATIONS

International Search Report dated Jul. 5, 2002.

\* cited by examiner

*Primary Examiner*—Cecilia J. Tsang
*Assistant Examiner*—Raymond Covington

(57) ABSTRACT

A process for preparing organic hydroperoxide having a reduced content of contaminants, which process involves:
(a) oxidation of an organic compound to obtain reaction product containing an organic hydroperoxide;
(b) contacting at least part of the organic hydroperoxide containing reaction product with a basic aqueous solution;
(c) separating the hydrocarbonaceous phase containing organic hydroperoxide from the aqueous phase;
(d) washing at least part of the separated hydrocarbonaceous phase containing organic hydroperoxide; and
(e) contacting at least part of the hydrocarbonaceous phase containing organic hydroperoxide with a guard bed having solid adsorbent with a void content of from 50% to 98% by volume.

8 Claims, No Drawings

PROCESS FOR PREPARING ORGANIC HYDROPEROXIDE HAVING A REDUCED AMOUNT OF CONTAMINANTS

FIELD OF THE INVENTION

The present invention relates to a process for preparing organic hydroperoxide having a reduced amount of contaminants. Such organic hydroperoxides can suitably be used in the preparation of propylene oxide.

BACKGROUND OF THE INVENTION

Processes for preparing propylene oxide with the help of organic hydroperoxides are well known in the art. As described in U.S. Pat. No. 5,883,268, such process conventionally comprises peroxidation of ethyl benzene, followed by contacting the peroxidation reaction product with aqueous base in amount sufficient to neutralize acidic components thereof, and phase separating the resulting mixture into separate aqueous and organic phases. The organic phase containing ethyl benzene hydroperoxide can be reacted with propylene catalyzed by solid heterogeneous catalyst in order to obtain propylene oxide. U.S. Pat. No. 5,883,268 describes that severe catalyst deactivation in the propene epoxidation is prevented by water washing the organic phase in order to separate off the basic materials followed by stripping water from the resulting organic phase.

U.S. Pat. No. 5,723,637 describes a similar process for producing propylene oxide comprising autoxidation of ethyl benzene to obtain a raw material solution of ethyl benzene hydroperoxide in ethyl benzene which is reacted with propylene in the presence of a titanium containing solid catalyst to give propylene oxide. In order to suppress depression of activity of the titanium containing solid catalyst with the passage of time, the raw material solution is prepared by washing the solution of ethyl benzene hydroperoxide in ethyl benzene with an aqueous alkali solution to bring the lactic acid concentration to 5 ppm by weight or less. The oily phase obtained after the alkali washing may further be washed with water.

It has been found that in spite of washing the organic hydroperoxide with a basic aqueous solution of an alkali metal salt optionally followed by a water wash, there is still a considerable amount of contaminants present in the product. It has been found that washing with a basic aqueous solution of a metal salt, introduces metal ions in the organic phase. The contaminants, especially the metal ions, can lead to problems when further processing the organic hydroperoxide. If the organic hydroperoxide is to be used in the preparation of propylene oxide, metal ions in the organic hydroperoxide stream can lead to more rapid deactivation of the catalyst generally applied for preparing propylene oxide from propene.

SUMMARY OF THE INVENTION

It has now surprisingly been found that the content of contaminants could especially easily and efficiently be reduced by contacting the hydrocarbonaceous phase containing organic hydroperoxide with a guard bed comprising solid adsorbent having a void content of from 50% to 98% by volume. If the organic peroxide is subsequently contacted with olefin, more specifically propene, and catalyst to obtain alkyl aryl hydroxide and propylene oxide, a marked reduction in deactivation of the catalyst was observed. The reduction in deactivation is highly surprising as the compounds in the reaction mixture are thought to be dissolved in the organic phase.

Therefore, the present invention relates to a process for preparing organic hydroperoxide having a reduced content of contaminants, which process comprises:
(a) oxidation of an organic compound to obtain reaction product containing an organic hydroperoxide,
(b) contacting at least part of the organic hydroperoxide containing reaction product with a basic aqueous solution,
(c) separating the hydrocarbonaceous phase containing organic hydroperoxide from the aqueous phase,
(d) washing at least part of the separated hydrocarbonaceous phase containing organic hydroperoxide, and
(e) contacting at least part of the hydrocarbonaceous phase containing organic hydroperoxide with a guard bed comprising solid adsorbent having a void content of from 50% to 98% by volume.

DETAILED DESCRIPTION OF THE INVENTION

Although the process of the present invention is described as a sequence of process steps, it is possible to carry out further process steps in between each of the process steps described. It is usual to separate off organic compounds which have not reacted during the process. This can be done at any time during the present process.

Organic hydroperoxides are useful in a range of processes. One of these processes is the reaction of organic hydroperoxide with an olefin containing from 3 to 10 carbon atoms, preferably from 3 to 6 carbon atoms, more preferably from 3 to 4 carbon atoms, most preferably propene, in order to obtain an oxirane compound containing the same number of carbon atoms as the starting olefin(s). In such process, the organic compound usually is an alkyl aryl. Such process further comprises:
(f) contacting at least part of the hydrocarbonaceous phase containing organic hydroperoxide obtained in step (e) with an olefin containing from 3 to 10 carbon and catalyst to obtain alkyl aryl hydroxide and an oxirane compound. Generally, such process will further comprise:
(g) separating at least part of the oxirane compound from the alkyl aryl hydroxide.

The alkyl aryl hydroxide obtained in step (g) can be used in a wide range of processes. One of these processes comprises the steps described above, and furthermore:
(h) dehydrating at least part of the alkyl aryl hydroxide obtained in step (g).

Although the organic compound used in the process of the present invention can in principle be any compound, organic compounds which are most frequently used are alkyl aryl compounds. Alkyl aryl compounds which are most frequently used are benzene compounds containing at least 1 alkyl substituent which alkyl substituent contains from 1 to 10 carbon atoms, preferably from 2 to 8 carbon atoms. Preferably, the benzene compound contains from 1 to 2 constituents. The alkyl aryl compounds most frequently used are ethyl benzene, di(iso-propyl)benzene and/or cumene.

The oxidation of the organic compound can be carried out by any suitable process known in the art. The oxidation can be carried out in the liquid phase in the presence of a diluent. This diluent is preferably a compound which is liquid under the reaction conditions and does not react with the starting materials and product obtained. However, the diluent can also be a compound necessarily present during the reaction. For example, if the alkyl aryl is ethyl benzene the diluent can be ethyl benzene as well.

The oxidation can conveniently be carried out by blowing air through the organic compound while cooling the reaction mixture in view of the exothermic nature of the reaction.

Besides the desired organic hydroperoxide, a wide range of contaminants can be formed during the oxidation of organic compounds. Although most of these are present in small amounts, it has been found that especially the presence of organic acids can cause problems in the further use of the organic hydroperoxides. As described in the prior art, a method of reducing the amount of contaminants is contacting the reaction product containing organic hydroperoxide with a basic aqueous solution, more specifically an aqueous solution of a metal salt, followed by further washing with water. However, the contact with the aqueous solution of a metal salt was observed to introduce metal ions into the organic hydroperoxide containing reaction product. Although the amount of organic acids can be decreased by washing with an aqueous solution of an alkali metal salt, the amount of alkali metal is usually increased.

It has been found that the process of the present invention is especially suitable for decreasing the metal content of the separated hydrocarbonaceous phase containing organic hydroperoxide obtained in step (c). The metal will usually be present in the form of metal ions. The process of the present invention is especially suitable for processes in which the basic aqueous solution is a basic aqueous solution of a metal salt.

In the process of the present invention, the organic hydroperoxide containing reaction product is contacted with a basic aqueous solution, more specifically a basic aqueous solution containing metal compounds. Although the metal compounds will frequently be metal salts, further metal compounds can be present as well. Suitable salts for use in the basic aqueous solution include alkali and alkaline earth metal salts. Preferably, alkali metal hydroxides, alkali metal carbonates and/or alkali metal hydrogen carbonates are used. Examples of these compounds are NaOH, KOH, $Na_2CO3$, $K_2CO_3$, $NaHCO_3$ and $KHCO_3$. In view of their easy availability, it is preferred to use NaOH and/or $Na_2CO_3$.

In commercial applications, at least part of the basic aqueous solution will usually be used again. Due to the presence of contaminants from previous washings, the basic aqueous solution used in step (b) in commercial applications can contain a wide range of compounds.

The speed by which the equilibrium is obtained in which the desired amount of contaminants is present in the aqueous phase, can be increased in the ways known to someone skilled in the art. Therefore, process step (b) is preferably carried out at elevated temperature and/or during intense mixing of the organic hydroperoxide containing reaction product and the basic aqueous solution. Such intense mixing can be done in any way known in the art. The exact conditions under which step (b) is carried out, strongly depends on the further circumstances.

After step (b), the hydrocarbonaceous phase is separated from the aqueous phase in step (c). A preferred method comprises allowing the hydrocarbonaceous phase and aqueous phase to settle, and subsequently removing part of all of one of the phases. Not all of the product obtained in step (b) needs to be subjected to step (c). However, preferably all product of step (b) is subjected to step (c).

In step (d), at least part of the separated hydrocarbonaceous phase obtained in step (c) is washed. Washing of the separated hydrocarbonaceous phase can be carried out in any way known to someone skilled in the art. The washing liquid is preferably water. However, the washing liquid can contain a wide range of further compounds as at least part of the water can have been used before either in the present process or in another process. Although used wash water can contain acidic compounds, there will usually be such mixture of compounds present that the pH of the washing liquid will be at least 7.5.

Washing of step (d) can be repeated as often as desired. Generally, the washing will be carried out from 1 to 5 times. It will be obvious that it is advantageous to limit the number of washing steps if possible.

In order to further reduce the number of contaminants, at least part of the hydrocarbonaceous phase containing organic hydroperoxide is subsequently contacted with a guard bed. Although part of the hydrocarbonaceous phase can be used, it will usually be preferred from an efficiency point of view to contact all of the hydrocarbonaceous phase. It was highly surprising that a bed comprising solid adsorbent having a void content of from 50% to 98% by volume, was capable of removing contaminants at least part of which are thought to be dissolved in the hydrocarbonaceous phase. However, it was found that adsorbents can remove the contaminants such that a substantially reduced pressure drop is observed when using the product obtained in step (e) in a further conversion step.

The void content of the solid adsorbent is considered to be the void volume between the solid particles. Potential pores inside the solid particles are not taken into account. The void content is based on total volume of solid adsorbent particles and volume between these particles. Preferably, the guard bed has a void content of at least 55% volume, more preferably at least 60%. The upper limit depends on the desired strength of the solid adsorbent particles. Usually, the void content can be at most 98%, more specifically at most 90%, most specifically at most 80%.

Many solid adsorbents are suitable for use in the present invention. It has been found that some adsorbents are less preferred than others in view of their reactivity towards the organic hydroperoxides. It is preferred that the solid adsorbent does not react to a substantial degree with the organic hydroperoxide. Therefore, the adsorbent is preferably an inert solid, more preferably one or more solids chosen from the group consisting of silica, silica gel, glass, alumina, more especially alpha-alumina, molecular sieves, clay and minerals.

In order to decrease any residual reactivity with the organic hydroperoxide which the solid might have, it is preferred that the solid adsorbent has a low surface area. Preferably, the surface area is less than 50 $m^2/g$, more preferably less than 20 $m^2/g$, most preferably less than 15 $m^2/g$.

The solid adsorbent can have any shape as long as the void content is obtained. The adsorbents used in the present invention can be shaped by extrusion. Further, it has been found that extrudates shaped as hollow cylinder particles give good results. In a preferred embodiment, the shapes of the solid adsorbent is such that it forms a graded guard bed. In a graded guard bed, larger solids with larger voids are present where the guard bed is first contacted with the hydrocarbonaceous phase containing organic hydroperoxide, while finer solid particles with smaller voids are present further down stream while the overall void content is at least 50%.

Although the guard bed can be present in a separate reactor, it is preferred from an economic point of view that the guard bed is on top of the catalyst bed in which the organic hydroperoxide is further converted.

In optional process step (f), at least part of the hydrocarbonaceous phase containing organic hydroperoxide obtained in step (e) is contacted with an olefin containing from 3 to 10 carbon atoms and catalyst to obtain alkyl aryl hydroxide and oxirane compound. A catalyst which can suitably used in such process comprises titanium on silica and/or silicate. A preferred catalyst is described in EP-A-345856 herein incorporated by reference. The reaction generally proceeds at moderate temperatures and pressures, in particular at temperatures in the range of from 0° C. to 200° C., preferably in the range from 25° C. to 200° C. The precise pressure is not critical as long as it suffices to maintain the reaction mixture in a liquid condition. Atmospheric pressure may be satisfactory. In general, pressures can be in the range of from 1 to $100 \times 10^5$ N/m$^2$.

At the conclusion of the epoxidation reaction, the liquid mixture comprising the desired products is separated from the catalyst. The oxirane compound can then be separated from the reaction product containing alkyl aryl hydroxide in any way known to be suitable to someone skilled in the art. The liquid reaction product may be worked up by fractional distillation, selective extraction and/or filtration. The solvent, the catalyst and any unreacted olefin or alkyl aryl hydroperoxide may be recycled or can be used in another process.

The alkyl aryl hydroxide obtained in the process can be dehydrated in the presence of a catalyst. Processes which can be used for this step have been described in WO 99/42425 herein incorporated by reference and WO 99/42426 herein incorporated by reference. However, any suitable process known to someone skilled can in principle be used.

I claim:

1. A process for preparing an organic hydroperoxide comprising:
   (a) oxidating an organic compound to obtain reaction product containing an organic hydroperoxide;
   (b) contacting at least part of the organic hydroperoxide containing reaction product with a basic aqueous solution;
   (c) separating the hydrocarbonaceous phase containing organic hydroperoxide from the aqueous phase;
   (d) washing at least part of the separated hydrocarbonaceous phase containing organic hydroperoxide; and,
   (e) contacting at least part of the hydrocarbonaceous phase containing organic hydroperoxide with a guard bed comprising solid adsorbent.

2. The process of claim 1, in which process the solid adsorbent has a void content of from 50% to 98% by volume.

3. The process of claim 1, in which process the organic compound is an alkyl aryl.

4. The process of claim 1, which process further comprises:
   (f) contacting at least part of the hydrocarbonaceous phase containing organic hydroperoxide obtained in step (e) with an olefin containing from 3 to 10 carbons and catalyst to obtain alkyl aryl hydroxide and an oxirane compound; and,
   (g) separating at least part of the oxirane compounds from the alkyl aryl hydroxide.

5. The process of claim 1, in which the basic aqueous solution further comprises metal compounds.

6. The process of claim 1, in which process the alkyl aryl is selected from the group consisting of ethyl benzene, di(isopropyl)benzene, cumene and any combination of these.

7. The process of claim 1, in which the solid adsorbent is one or more solids chosen from the group consisting of silica, silica gel, glass, alumina, molecular sieves, clay and minerals.

8. The process of claim 1, in which the solids in the guard bed have a void content of from 55% to 90% by volume.

* * * * *